US011759311B2

(12) United States Patent
Whitsett (10) Patent No.: US 11,759,311 B2
(45) Date of Patent: Sep. 19, 2023

(54) EXCHANGEABLE LENS PLATFORM

(71) Applicant: Jeffrey Whitsett, Houston, TX (US)

(72) Inventor: Jeffrey Whitsett, Houston, TX (US)

( * ) Notice: Subject to any disclaimer, the term of this patent is extended or adjusted under 35 U.S.C. 154(b) by 112 days.

(21) Appl. No.: 17/171,558

(22) Filed: Feb. 9, 2021

(65) Prior Publication Data

US 2021/0244531 A1 Aug. 12, 2021

Related U.S. Application Data

(60) Provisional application No. 62/972,014, filed on Feb. 9, 2020.

(51) Int. Cl.
*A61F 2/16* (2006.01)

(52) U.S. Cl.
CPC .............. *A61F 2/1648* (2013.01); *A61F 2/16* (2013.01); *A61F 2/1694* (2013.01);
(Continued)

(58) Field of Classification Search
CPC .... A61F 2/1613; A61F 2/1648; A61F 2/1694; A61F 2002/169; A61F 2002/16901; A61F 2002/16902
See application file for complete search history.

(56) References Cited

U.S. PATENT DOCUMENTS 5,628,795 A * 5/1997 Langerman ........... A61F 2/1694
   623/4.1
6,797,004 B1 * 9/2004 Brady ................... A61F 2/1629
   623/6.38

(Continued)

FOREIGN PATENT DOCUMENTS

GB 2171912 9/1986

OTHER PUBLICATIONS

Indications and Clinical Outcome of CTR Implantation, Mar. 1, 2007 https://www.ncbi.nlm.nih.gov/pmc/articles/PMC2699984/.
(Continued)

*Primary Examiner* — William H Matthews
(74) *Attorney, Agent, or Firm* — LAW OFFICES OF STEVEN W. WEINRIEB (57) ABSTRACT

An exchangeable lens platform (ELP) comprises a horseshoe-shaped ring structure, which has a memory strip incorporated therein, into which the haptic end components of the intraocular lens (IOL) can engage diametrically opposite portions of the ring structure. In this manner, the exchangeable lens platform (ELP) can not only be opened or expanded so as to be disposed within any sized capsular bag in a secure and stabilized manner, but diametrically opposite portions of the exchangeable lens platform (ELP) can effectively fold upon themselves such that the exchangeable lens platform (ELP) will effectively be partially folded in half such that the diametrically opposite folded portions of the exchangeable lens platform (ELP) can effectively engage diametrically opposed internal wall portions of the fornix of the capsular bag so as to permit the intraocular lens (IOL) to then be properly centered, oriented, stabilized, and secured within the eye. In addition, since the haptic components of the intraocular lens (IOL) are disposed upon the exchangeable lens platform (ELP) and do not engage internal peripheral wall portions of the capsular bag, the intraocular lens (IOL) can be removed and replaced with another intraocular lens (IOL).

19 Claims, 4 Drawing Sheets

(52) U.S. Cl.
CPC .. *A61F 2002/169* (2015.04); *A61F 2002/1689* (2013.01); *A61F 2210/0014* (2013.01)

(56) References Cited

U.S. PATENT DOCUMENTS

| | | | |
|---|---|---|---|
| 7,025,783 | B2 | 4/2006 | Brady et al. |
| 7,029,497 | B2 | 4/2006 | Zhang et al. |
| 8,728,158 | B2 | 5/2014 | Whitsett |
| 8,852,275 | B2 | 10/2014 | Park |
| 8,920,495 | B2 | 12/2014 | Mirlay |
| 9,339,375 | B2 | 5/2016 | Lee et al. |
| 10,111,746 | B2 | 10/2018 | Wortz et al. |
| 10,271,945 | B2 | 4/2019 | Wortz et al. |
| 10,548,714 | B2 | 2/2020 | Sri |
| 10,799,340 | B2 | 10/2020 | Collins et al. |
| 2005/0085907 | A1 | 4/2005 | Hanna |
| 2006/0235515 | A1 | 10/2006 | Chassain |
| 2008/0281415 | A1 | 11/2008 | Cumming |
| 2011/0160853 | A1 | 6/2011 | Scholten |
| 2016/0022488 | A1 | 1/2016 | Dimmig et al. |
| 2019/0021849 | A1 | 1/2019 | Dolla |
| 2019/0117382 | A1* | 4/2019 | Kahook ................ A61F 9/0017 |

OTHER PUBLICATIONS

Closed Foldable Capsular Rings, Mar. 2005 https://sci-hub.st/https://pubmed.ncbi.nlm.nih.gov/15811732/.
Tension Rings.

* cited by examiner

EXCHANGEABLE LENS PLATFORM

CROSS-REFERENCE TO RELATED PATENT APPLICATIONS

This patent application is a non-provisional patent application based upon U.S. Provisional Patent Application No. 62/972,014 which was filed on Feb. 9, 2020, the priority benefits of which are hereby claimed.

FIELD OF THE INVENTION

The present invention relates generally to medical equipment, and more particularly to a new and improved exchangeable lens platform (ELP) which is to be utilized in connection with the implantation of an intraocular lens (IOL) during cataract surgery. Still more particularly, the new and improved exchangeable lens platform (ELP) effectively comprises a horseshoe-shaped ring structure comprised of superior and inferior arcuate portions which form a discontinuous curvilinear structure, which has a memory strip incorporated therein, into which the haptic end components of the intraocular lens (IOL) can engage diametrically opposite portions of the ring structure whereby the new and improved exchangeable lens platform (ELP) can not only be opened or expanded so as to be disposed within any sized capsular bag in a secure and stabilized manner, but the diametrically opposite arcuate portions of the new and improved exchangeable lens platform (ELP) can effectively fold upon themselves such that the new and improved exchangeable lens platform (ELP) will effectively be partially folded in such a manner that the diametrically opposite folded portions of the new and improved exchangeable lens platform (ELP) can effectively engage diametrically opposed internal wall portions of the fornix of the capsular bag so as to permit the intraocular lens (IOL) to then be properly centered, oriented, stabilized, and secured within the eye.

BACKGROUND OF THE INVENTION

With modern advancements in cataract surgery techniques and technology, intraocular lenses (IOLs) are routinely implanted within a patient's eye so as to correct various refractive deficiencies in a patient's eye, such as, for example, myopia, hyperopia, and astigmatism, which may develop as a patient ages. In the case of astigmatism, for example, which is a common occurrence in patients wherein, in lieu of the cornea, for example, being perfectly spherical, the cornea is asymmetric such that, in effect, the cornea is somewhat elliptical whereby one axis has a greater radius of curvature. In such an instance, a toric intraocular lens (IOL) is used to correct the astigmatism. More particularly, after the patient's original crystalline lens has been removed during cataract surgery, usually by customary phacoemulsification techniques, a toric intraocular lens (IOL), of known power to correct the vision in an aphakic eye, is inserted into the capsular bag and rotated to a particular vector orientation relative to the capsular bag, as well as with respect to the cornea, such that the clinical effects of the astigmatism can be neutralized. It is of course to be noted that other intraocular lenses (IOLs) can be utilized depending upon the particular medical condition of the patient to be addressed.

Current intraocular lenses (IOLs) often comprise an optically clear lens and flexible haptic components which extend substantially radially outwardly from diametrically opposite ends or sides of the lens and can have various different configurations so as to securely seat the lens within the capsular bag of the eye. In addition, it is known that since the support structure of the human eye can vary, various different platforms have therefore been developed so as to support the intraocular lens (IOL) whereby, when the intraocular lens (IOL) is inserted into the capsular bag of the eye, the intraocular lens (IOL) can be properly centered, stabilized, and oriented within the eye. Subsequent to the implantation of the intraocular lens (IOL) into the eye, tissue growth and fibrosis occur around the haptic components so as to effectively secure or "glue" the intraocular lens (IOL) in place within the eye, over time. Unfortunately, current support platforms are not readily utilized within the eyes of different patients, or more particularly, within the capsular bags of the eyes of different patients, due to the diversity of structure, size, and configuration comprising the capsular bags of different human eyes. Still further, once tissue growth and fibrosis occur around the haptic and optic components of the intraocular lens (IOL), it is extremely difficult, and nearly impossible, to safely remove the intraocular lens (IOL) without damage thereto, or more importantly, without damaging critically important regions of the patient's eye.

A need therefore exists in the art for a new and improved exchangeable lens platform (ELP) for use in connection with the proper support, fixation, and orientation of an intraocular lens (IOL) within the human eye. Another need exists in the art for a new and improved exchangeable lens platform (ELP) for use in connection with the proper support, fixation, and orientation of an intraocular lens (IOL) within the human eye, and wherein the new and improved exchangeable lens platform (ELP) can be easily inserted into the eye by the anterior segment surgeon performing, for example, cataract surgery upon a patient. An additional need exists in the art for a new and improved exchangeable lens platform (ELP) for use in connection with the proper support, fixation, and orientation of an intraocular lens (IOL) within the human eye, wherein the new and improved exchangeable lens platform (ELP) can be easily inserted into the eye by the anterior segment surgeon performing, for example, cataract surgery upon a patient, and wherein the new and improved exchangeable lens platform (ELP) can be utilized within various, differently sized, or differently shaped, capsular bags of different human eyes. A further need exists in the art for a new and improved exchangeable lens platform (ELP) for use in connection with the proper support, fixation, and orientation of an intraocular lens (IOL) within the human eye, wherein the new and improved exchangeable lens platform (ELP) can be easily inserted into the eye by the anterior segment surgeon performing, for example, cataract surgery upon a patient, wherein the new and improved exchangeable lens platform (ELP) can be utilized within various, differently sized, or differently shaped, capsular bags of different human eyes, and wherein the new and improved exchangeable lens platform (ELP) will automatically accommodate itself to the particular size and/or shape of the capsular bag within which the new and improved exchangeable lens platform (ELP) is being inserted.

A yet further need exists in the art for a new and improved exchangeable lens platform (ELP) for use in connection with the proper support, fixation, and orientation of an intraocular lens (IOL) within the human eye, wherein the new and improved exchangeable lens platform (ELP) can be easily inserted into the eye by the anterior segment surgeon performing, for example, cataract surgery upon a patient, wherein the new and improved exchangeable lens platform (ELP) can be utilized within various, differently sized, or differently shaped, capsular bags of different human eyes, wherein the new and improved exchangeable lens platform (ELP) will automatically accommodate itself to the particular size and/or shape of the capsular bag within which the new and improved exchangeable lens platform (ELP) is being inserted, and wherein, when the intraocular lens is inserted into the eye by the anterior segment surgeon performing, for example, cataract surgery upon a patient, the haptic components of the intraocular lens (IOL) will be readily accommodated within the new and improved exchangeable lens platform (ELP). A still further need exists in the art for a new and improved exchangeable lens platform (ELP) for use in connection with the proper support, fixation, and orientation of an intraocular lens (IOL) within the human eye, wherein the new and improved exchangeable lens platform (ELP) can be easily inserted into the eye by the anterior segment surgeon performing, for example, cataract surgery upon a patient, wherein the new and improved exchangeable lens platform (ELP) can be utilized within various, differently sized, or differently shaped, capsular bags of different human eyes, wherein the new and improved exchangeable lens platform (ELP) will automatically accommodate itself to the particular size and/or shape of the capsular bag within which the new and improved exchangeable lens platform (ELP) is being inserted, wherein, when the intraocular lens is inserted into the eye by the anterior segment surgeon performing, for example, cataract surgery upon a patient, the haptic components of the intraocular lens (IOL) will be readily accommodated within the new and improved exchangeable lens platform (ELP), and wherein diametrically opposed regions of the new and improved exchangeable lens platform (ELP) will effectively partially fold upon themselves such that upper and lower arcuate portions of the new and improved exchangeable lens platform (ELP) will effectively come together whereby apex portions of such folded regions of the new and improved exchangeable lens platform (ELP) can effectively be fixedly disposed or accommodated within diametrically opposed fornix regions of the capsular bag.

A yet still further need exists in the art for a new and improved exchangeable lens platform (ELP) for use in connection with the proper support, fixation, and orientation of an intraocular lens (IOL) within the human eyes, wherein the new and improved exchangeable lens platform (ELP) can be easily inserted into the eye by the anterior segment surgeon performing, for example, cataract surgery upon a patient, wherein the new and improved exchangeable lens platform (ELP) can be utilized within various, differently sized, or differently shaped, capsular bags, wherein the new and improved exchangeable lens platform (ELP) will automatically accommodate itself to the particular size and/or shape of the capsular bag of the particular eye into which the intraocular lens (IOL) is being inserted, wherein, when the intraocular lens (IOL) is inserted into the eye by the anterior segment surgeon performing, for example, cataract surgery upon a patient, the haptic components of the intraocular lens (IOL) will be readily accommodated within the new and improved exchangeable lens platform (ELP), wherein diametrically opposed regions of the new and improved exchangeable lens platform (ELP) will effectively partially fold upon themselves such that upper and lower arcuate portions of the new and improved exchangeable lens platform (ELP) will effectively come together whereby apex portions of such folded regions of the new and improved exchangeable lens platform (ELP) can effectively be fixedly disposed or accommodated within diametrically opposed fornix regions of the capsular bag, within which the haptic components of the intraocular lens (IOL) will be disposed, such that the haptic components of the intraocular lens (IOL) will effectively be captured within the apex portions of the new and improved exchangeable lens platform (ELP) whereby the new and improved exchangeable lens platform (ELP) will effectively define a stable platform for the intraocular lens (IOL), by reducing contact to the haptic and optical structures of the intraocular lens (IOL), as well as to the intraocular lens (IOL) itself, by the anterior and posterior portions of the capsular bag, such that the haptic portions of the intraocular lens (IOL) will be stabilized so as to prevent them from moving either side to side or circumferentially within the exchangeable lens platform (ELP).

A last need exists in the art for a new and improved exchangeable lens platform (ELP) for use in connection with the proper support, fixation, and orientation of an intraocular lens (IOL) within the human eyes, wherein the new and improved exchangeable lens platform (ELP) can be easily inserted into the eye by the anterior segment surgeon performing, for example, cataract surgery upon a patient, wherein the new and improved exchangeable lens platform (ELP) can be utilized within various, differently sized, or differently shaped, capsular bags, wherein the new and improved exchangeable lens platform (ELP) will automatically accommodate itself to the particular size and/or shape of the capsular bag of the particular eye into which the intraocular lens (IOL) is being inserted, wherein, when the intraocular lens (IOL) is inserted into the eye by the anterior segment surgeon performing, for example, cataract surgery upon a patient, the haptic components of the intraocular lens (IOL) will be readily accommodated within the new and improved exchangeable lens platform (ELP), wherein diametrically opposed regions of the new and improved exchangeable lens platform (ELP) will effectively partially fold upon themselves such that upper and lower arcuate portions of the new and improved exchangeable lens platform (ELP) will effectively come together whereby apex portions of such folded regions of the new and improved exchangeable lens platform (ELP) can effectively be fixedly disposed or accommodated within diametrically opposed fornix regions of the capsular bag, within which the haptic components of the intraocular lens (IOL) will be disposed, such that the haptic components of the intraocular lens (IOL) will effectively be captured within the apex portions of the new and improved exchangeable lens platform (ELP) whereby the new and improved exchangeable lens platform (ELP) will effectively define a stable platform for the intraocular lens (IOL) such that the haptic portions of the intraocular lens (IOL), as well as the intraocular lens (IOL) itself, will be prevented from moving from side to side or circumferentially within the exchangeable lens platform (ELP), and wherein, since the intraocular lens (IOL), and more particularly, the haptic components thereof, are mounted upon the a new and improved exchangeable lens platform (ELP), tissue growth and fibrosis will effectively be inhibited, thereby preventing such from engaging or entangling the haptic components of the intraocular lens (IOL) such that contrary to conventionally implanted intraocular lenses (IOLs), the intraocular lens can be removed from the patients eye and replaced with a new or different intraocular lens (IOL) which may comprise an intraocular lens having a different configuration or curvature, a different visual corrective power, or the like.

OVERALL OBJECTIVES OF THE PRESENT INVENTION

Therefore, an overall objective of the present invention is to provide a new and improved exchangeable lens platform (ELP) for use in connection with the proper support, fixation, and orientation of an intraocular lens (IOL) within the human eye. Another overall objective of the present invention is to provide a new and improved exchangeable lens platform (ELP) for use in connection with the proper support, fixation, and orientation of an intraocular lens (IOL) within the human eye, and wherein the new and improved exchangeable lens platform (ELP) can be easily inserted into the eye by the anterior segment surgeon performing, for example, cataract surgery upon a patient. An additional overall objective of the present invention is to provide a new and improved exchangeable lens platform (ELP) for use in connection with the proper support, fixation, and orientation of an intraocular lens (IOL) within the human eye, wherein the new and improved exchangeable lens platform (ELP) can be easily inserted into the eye by the anterior segment surgeon performing, for example, cataract surgery upon a patient, and wherein the new and improved exchangeable lens platform (ELP) can be utilized within various, differently sized, or differently shaped, capsular bags of different human eyes. A further overall objective of the present invention is to provide a new and improved exchangeable lens platform (ELP) for use in connection with the proper support, fixation, and orientation of an intraocular lens (IOL) within the human eye, wherein the new and improved exchangeable lens platform (ELP) can be easily inserted into the eye by the anterior segment surgeon performing, for example, cataract surgery upon a patient, wherein the new and improved exchangeable lens platform (ELP) can be utilized within various, differently sized, or differently shaped, capsular bags of different human eyes, and wherein the new and improved exchangeable lens platform (ELP) will automatically accommodate itself to the particular size and/or shape of the capsular bag within which the new and improved exchangeable lens platform (ELP) is being inserted.

A yet further overall objective of the present invention is to provide a new and improved exchangeable lens platform (ELP) for use in connection with the proper support, fixation, and orientation of an intraocular lens (IOL) within the human eye, wherein the new and improved exchangeable lens platform (ELP) can be easily inserted into the eye by the anterior segment surgeon performing, for example, cataract surgery upon a patient, wherein the new and improved exchangeable lens platform (ELP) can be utilized within various, differently sized, or differently shaped, capsular bags of different human eyes, wherein the new and improved exchangeable lens platform (ELP) will automatically accommodate itself to the particular size and/or shape of the capsular bag within which the new and improved exchangeable lens platform (ELP) is being inserted, and wherein, when the intraocular lens is inserted into the eye by the anterior segment surgeon performing, for example, cataract surgery upon a patient, the haptic components of the intraocular lens (IOL) will be readily accommodated within the new and improved exchangeable lens platform (ELP).

A still further overall objective of the present invention is to provide a new and improved exchangeable lens platform (ELP) for use in connection with the proper support, fixation, and orientation of an intraocular lens (IOL) within the human eye, wherein the new and improved exchangeable lens platform (ELP) can be easily inserted into the eye by the anterior segment surgeon performing, for example, cataract surgery upon a patient, wherein the new and improved exchangeable lens platform (ELP) can be utilized within various, differently sized, or differently shaped, capsular bags of different human eyes, wherein the new and improved exchangeable lens platform (ELP) will automatically accommodate itself to the particular size and/or shape of the capsular bag within which the new and improved exchangeable lens platform (ELP) is being inserted, wherein, when the intraocular lens is inserted into the eye by the anterior segment surgeon performing, for example, cataract surgery upon a patient, the haptic components of the intraocular lens (IOL) will be readily accommodated within the new and improved exchangeable lens platform (ELP), and wherein diametrically opposed regions of the new and improved exchangeable lens platform (ELP) will effectively partially fold upon themselves such that upper and lower arcuate portions of the new and improved exchangeable lens platform (ELP) will effectively come together whereby apex portions of such folded regions of the new and improved exchangeable lens platform (ELP) can effectively be fixedly disposed or accommodated within diametrically opposed fornix regions of the capsular bag.

A yet still further overall objective of the present invention is to provide a new and improved exchangeable lens platform (ELP) for use in connection with the proper support, fixation, and orientation of an intraocular lens (IOL) within the human eyes, wherein the new and improved exchangeable lens platform (ELP) can be easily inserted into the eye by the anterior segment surgeon performing, for example, cataract surgery upon a patient, wherein the new and improved exchangeable lens platform (ELP) can be utilized within various, differently sized, or differently shaped, capsular bags, wherein the new and improved exchangeable lens platform (ELP) will automatically accommodate itself to the particular size and/or shape of the capsular bag of the particular eye into which the intraocular lens (IOL) is being inserted, wherein, when the intraocular lens (IOL) is inserted into the eye by the anterior segment surgeon performing, for example, cataract surgery upon a patient, the haptic components of the intraocular lens (IOL) will be readily accommodated within the new and improved exchangeable lens platform (ELP), wherein diametrically opposed regions of the new and improved exchangeable lens platform (ELP) will effectively partially fold upon themselves such that upper and lower arcuate portions of the new and improved exchangeable lens platform (ELP) will effectively come together whereby apex portions of such folded regions of the new and improved exchangeable lens platform (ELP) can effectively be fixedly disposed or accommodated within diametrically opposed fornix regions of the capsular bag, within which the haptic components of the intraocular lens (IOL) will be disposed, such that the haptic components of the intraocular lens (IOL) will effectively be captured within the apex portions of the new and improved exchangeable lens platform (ELP) whereby the new and improved exchangeable lens platform (ELP) will effectively define a stable platform for the intraocular lens (IOL) such that the haptic portions of the intraocular lens (IOL), as well as the intraocular lens (IOL) itself, will be stabilized, thereby preventing it from moving from side to side or circumferentially within the exchangeable lens platform (ELP).

A last overall objective of the present invention is to provide a new and improved exchangeable lens platform (ELP) for use in connection with the proper support, fixation, and orientation of an intraocular lens (IOL) within the human eyes, wherein the new and improved exchangeable lens platform (ELP) can be easily inserted into the eye by the anterior segment surgeon performing, for example, cataract surgery upon a patient, wherein the new and improved exchangeable lens platform (ELP) can be utilized within various, differently sized, or differently shaped, capsular bags, wherein the new and improved exchangeable lens platform (ELP) will automatically accommodate itself to the particular size and/or shape of the capsular bag of the particular eye into which the intraocular lens (IOL) is being inserted, wherein, when the intraocular lens (IOL) is inserted into the eye by the anterior segment surgeon performing, for example, cataract surgery upon a patient, the haptic components of the intraocular lens (IOL) will be readily accommodated within the new and improved exchangeable lens platform (ELP), wherein diametrically opposed regions of the new and improved exchangeable lens platform (ELP) will effectively partially fold upon themselves such that upper and lower arcuate portions of the new and improved exchangeable lens platform (ELP) will effectively come together whereby apex portions of such folded regions of the new and improved exchangeable lens platform (ELP) can effectively be fixedly disposed or accommodated within diametrically opposed fornix regions of the capsular bag, within which the haptic components of the intraocular lens (IOL) will be disposed, such that the haptic components of the intraocular lens (IOL) will effectively be captured within the apex portions of the new and improved exchangeable lens platform (ELP) whereby the new and improved exchangeable lens platform (ELP) will effectively define a stable platform for the intraocular lens (IOL) such that the haptic portions of the intraocular lens (IOL), as well as the intraocular lens (IOL) itself, will be prevented from moving from side to side or circumferentially within the exchangeable lens platform (ELP), and wherein, since the intraocular lens (IOL), and more particularly, the haptic components thereof, are mounted upon the a new and improved exchangeable lens platform (ELP), tissue growth and fibrosis will effectively be inhibited, thereby preventing such from engaging or entangling the haptic components of the intraocular lens (IOL) such that contrary to conventionally implanted intraocular lenses (IOLs), the intraocular lens can be removed from the patient's eye and replaced with a new or different intraocular lens (IOL) which may comprise an intraocular lens having a different configuration or curvature, a different visual corrective power, or the like.

BRIEF DESCRIPTION OF THE DRAWINGS

Various other features and attendant advantages of the present invention will be more fully appreciated from the following detailed description when considered in connection with the accompanying drawing wherein:

FIG. 4 is a schematic perspective view of a new and improved exchangeable lens platform (ELP) which has been developed in accordance with the principles and teachings of the present invention, which has a substantially horseshoe-shaped configuration, which is provided with a substantially circumferential groove or track defined along the inner periphery thereof and within which diametrically opposed portions thereof can be engaged by the diametrically opposed, outwardly extending haptic components of the intraocular lens (IOL), wherein the exchangeable lens platform (ELP) is adapted to fold upon itself such that upper and lower arcuate portions of the new and improved exchangeable lens platform (ELP) will effectively approach each other whereby apex portions of such folded regions of the new and improved exchangeable lens platform (ELP) can effectively be fixedly disposed or accommodated within diametrically opposed fornix regions of the capsular bag, and wherein further, the haptic components of the intraocular lens (IOL) will be disposed within such apex portions of the diametrically opposed folded regions of the new and improved exchangeable lens platform (ELP) whereby the new and improved exchangeable lens platform (ELP) will effectively define a stable platform for the intraocular lens (IOL) which will now be properly seated, centered, stabilized, and oriented within the eye;

DETAILED DESCRIPTION OF THE PRESENT INVENTION

Figure 1:
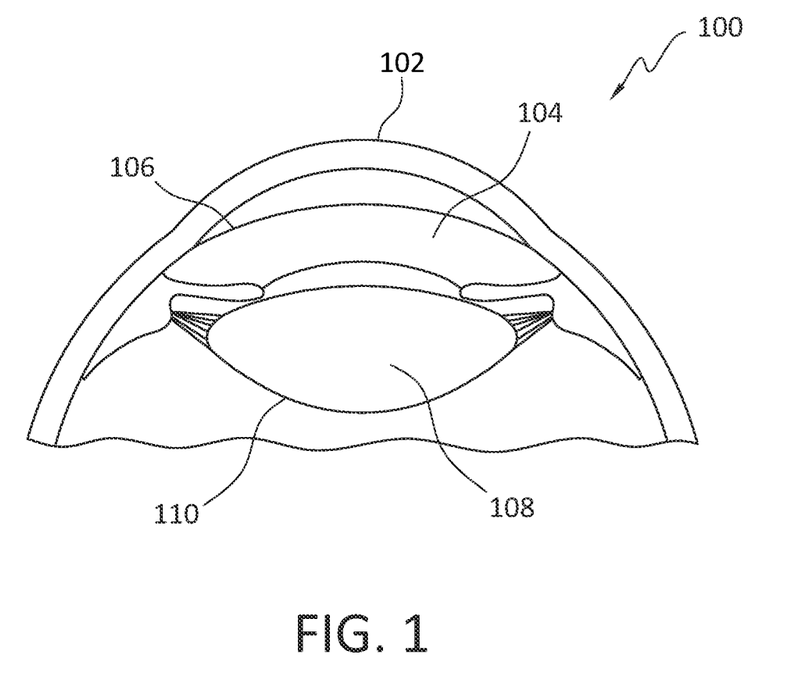
FIG. 1 is a cross-section of a human eye disclosing the various structural components of the human eye.
Figures 2, 3:
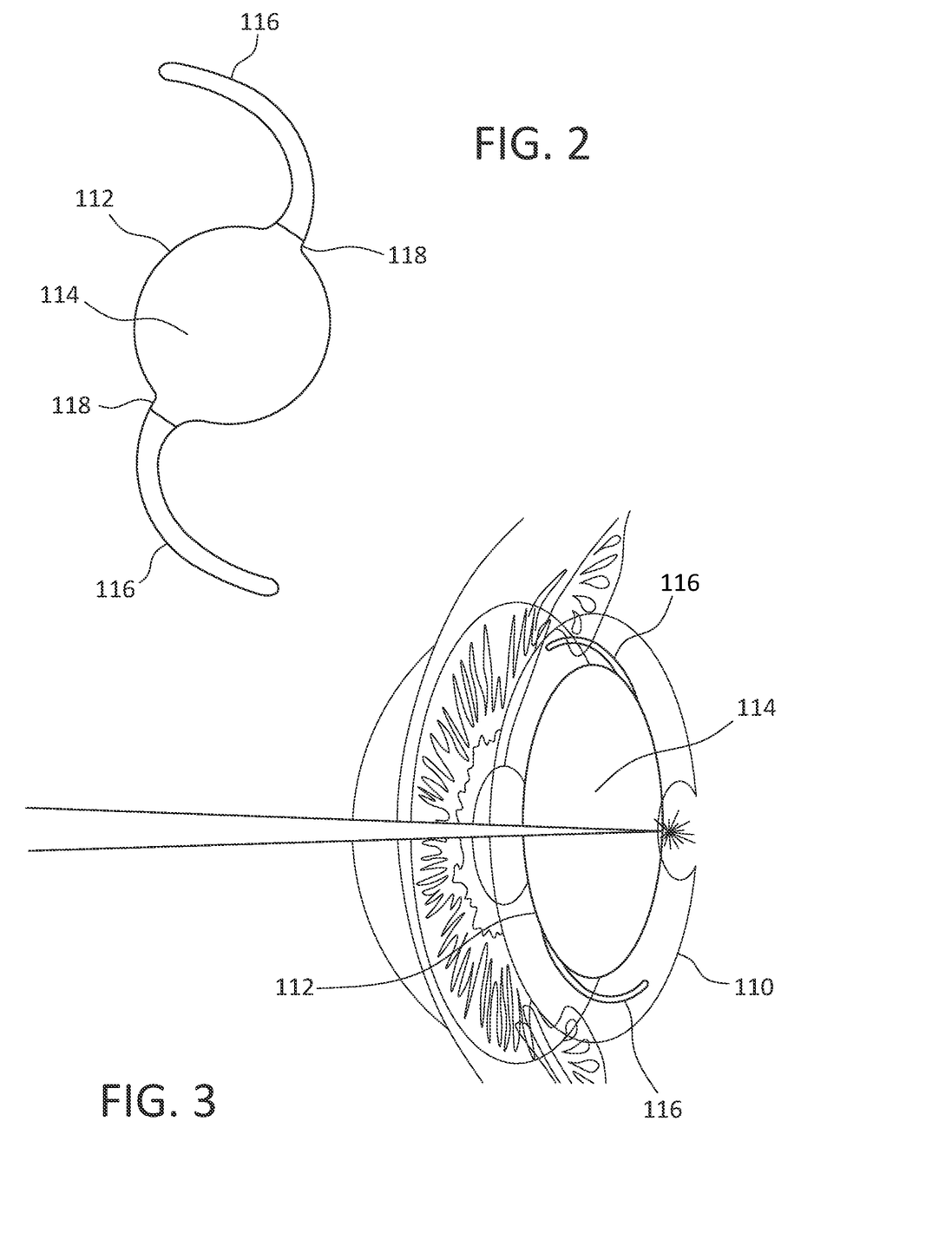
FIG. 2 is a plan view of an intraocular lens (IOL) showing the haptics, optic, and the haptic/optic junctions.
FIG. 3 is a cross-section of a human eye having an intraocular lens (IOL) inserted into the capsular bag.
Figure 4:
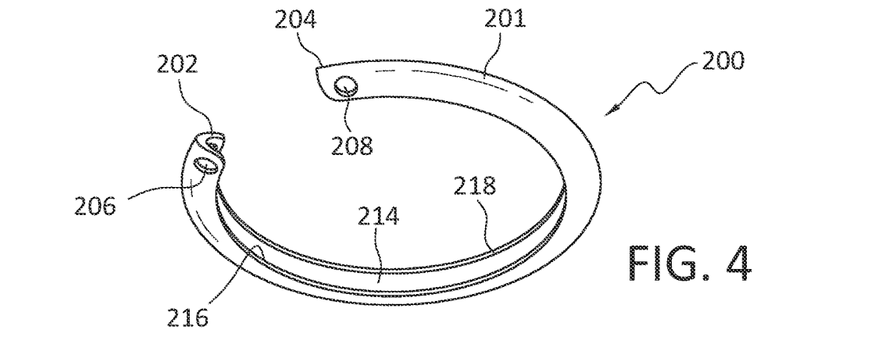

With reference being firstly made to FIGS. 1-3, a cross-section of a human eye is illustrated for background purposes and is generally indicated by the reference character 100. As is illustrated, it is seen that the human eye 100 comprises, among other components, the cornea 102, the iris 104, the pupil 106, and the natural crystalline lens 108 disposed within the capsular bag 110. As a result of cataract surgery, as has been described briefly hereinbefore, the lens 108 will be removed and an intraocular lens (IOL) 112 will effectively be substituted for the lens 108 when inserted into the capsular bag 110 by means of the anterior segment surgeon performing the cataract surgery. The disposition of the intraocular lens (IOL) 112 within the capsular bag 110 is illustrated within FIG. 3. As can be appreciated from FIGS. 2 and 3, the intraocular lens (IOL) 112 comprises a central optic component 114 and a pair of curved haptic components 116, 116 which extend outwardly from diametrically opposite locations of the circumferential periphery of the central optic component 114 so as to effectively extend in opposite directions and to define with the central optic component 114 of the intraocular lens (IOL) 112, haptic/optic junctions 118, 118. The haptic components 116, 116 effectively define flexible arms such that when the intraocular lens (IOL) 112 is inserted into the capsular bag 110, the haptic components 116, 116 will be forced radially inwardly toward the axis of the intraocular lens (IOL) 112 such that the haptic components 116, 116 will always attempt to spring back to their original unbiased positions so as to attempt to engage the internal wall portion of the capsular bag 110 with a predetermined amount of biasing force. As may be appreciated, however, it can be anticipated that the intraocular lens (IOL) assembly, comprising the central optic component 114 and the haptic components 116, can conceivably move circumferentially within the capsular bag 110 such that the intraocular lens (IOL) assembly is not immediately fixedly secured within the capsular bag. The new and improved exchangeable lens platform (ELP) has been developed in accordance with the principles and teachings of the present invention in order to address this precise problem.

Figure 10:
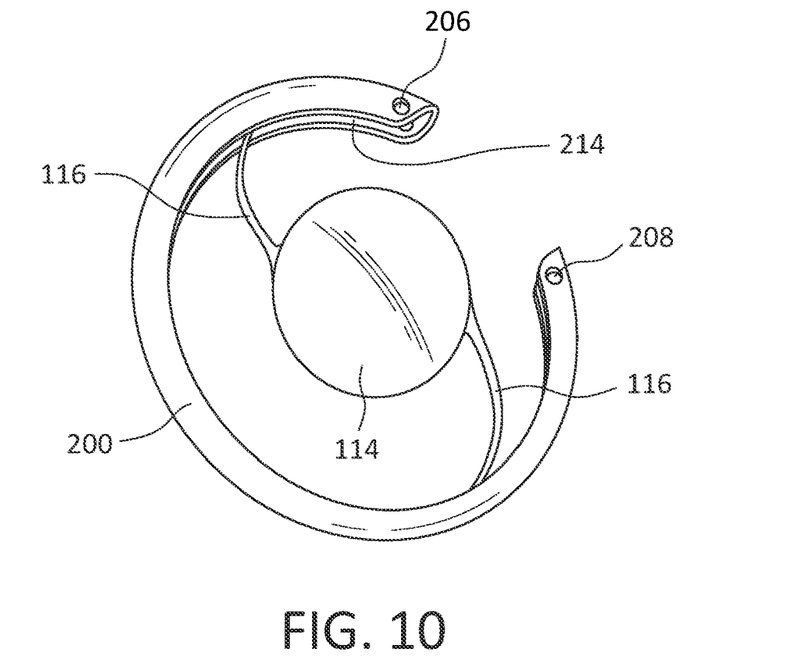
FIG. 10 is perspective view showing an intraocular lens (IOL) with the haptic components thereof disposed within the substantially circumferential groove or track defined along the inner periphery of the new and improved exchangeable lens platform (ELP) when, of course, the intraocular lens (IOL) and the new and improved exchangeable lens platform (ELP) are not disposed within the capsular bag of the human eye.

With reference therefore now being made to FIGS. 4-9, a new and improved exchangeable lens platform (ELP) is illustrated and is generally indicated by the reference character 200. As is illustrated, it is seen that the new and improved exchangeable lens platform (ELP) 200 has a substantially circular configuration which effectively forms a ring member 201, except that two, oppositely disposed end portions 202, 204 of the ring 201 are spaced from each other such that the ring member 201 defines a discontinuous substantially horseshoe configuration. More particularly, it is noted that the ring 201 effectively encompasses a circular locus of approximately 340°. In addition, each end 202, 204 of the ring 201 is provided with an aperture 206, 208 which enables the ring 201 to be manipulated by means of the cataract surgeon using a suitable tool, not shown, so as to insert the ring 201 into a linearly extending cartridge 210 of a suitable delivery device 212 as illustrated within FIG. 11. The two holes or apertures 206, 208 are provided for the convenience of the particular surgeon, that is, a particular surgeon may prefer a right-handed or left-handed delivery, and therefore chooses to manipulate the ring 200 by using either his right hand or left hand, whichever is most preferable. In addition, the new and improved exchangeable lens platform (ELP) 200 is preferably fabricated from a suitable material, such as, for example, a thin section of polyamide, or a material with similar properties that comprises a medical grade, FDA-approved material, such as, for example, a suitable silicone material or the like, such that the new and improved exchangeable lens platform (ELP) 200 is flexible and resilient, and has a diametrical extent which has a radius of curvature larger than that of the capsular bag 110. For these reasons, the substantially circular configuration of the new and improved exchangeable lens platform (ELP) 200 permits the new and improved exchangeable lens platform (ELP) 200 to effectively contract within its plane so as to be readily and easily accommodated within differently sized or differently shaped capsular bags, and yet exhibit a predetermined amount of radially outwardly oriented expansible force which permits the new and improved exchangeable lens platform (ELP) 200 to effectively locate and anchor itself within the fornix or equatorial region of the capsular bag. It is lastly seen from FIG. 4 that the new and improved horseshoe-shaped exchangeable lens platform (ELP) 200 has a groove or track 214 defined around the entire inner periphery of the new and improved horseshoe-shaped exchangeable lens platform (ELP) 200, and that the track or groove 214 has radially inwardly extending sidewall portions 216, 218 within which the haptic components 116, 116 of the intraocular lens (IOL) 112 can be inserted after the new and improved exchangeable lens platform (ELP) 200 has been inserted into the patient's eye. This relative disposition between the intraocular lens (IOL) 112, and more particularly the haptic components 116, 116 thereof, and the new and improved exchangeable lens platform (ELP) 200, can be best appreciated from FIG. 10.

Figure 5:
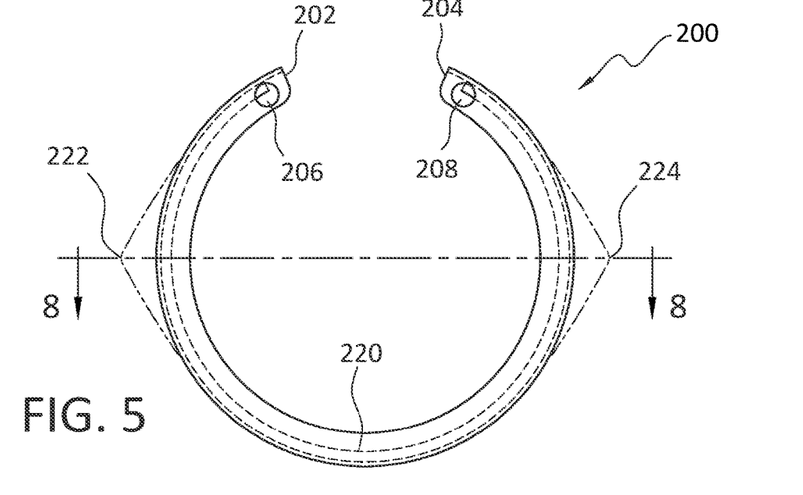
FIG. 5 is a schematic front elevational view of the new and improved exchangeable lens platform (ELP) shown in FIG. 4.
Figure 6:
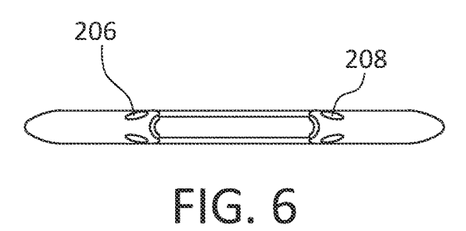
FIG. 6 is a schematic front elevational view of the new and improved exchangeable lens platform (ELP) shown in FIGS. 4 and 5.
Figure 7:
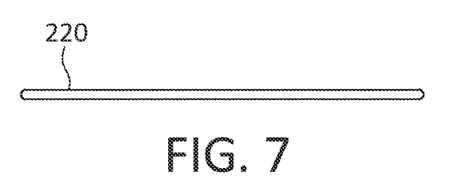
FIG. 7 is a schematic view of a flexible memory strip that is incorporated within the new and improved exchangeable lens platform (ELP), as shown in FIG. 5, so as to extend around substantially the entire arcuate extent of the new and improved exchangeable lens platform (ELP) and thereby provide the new and improved exchangeable lens platform (ELP) with its inherent flexibility and memory so as to attain and retain the particular, unbiased, horseshoe-shaped configuration thereof as shown in FIG. 5.
Figure 8:
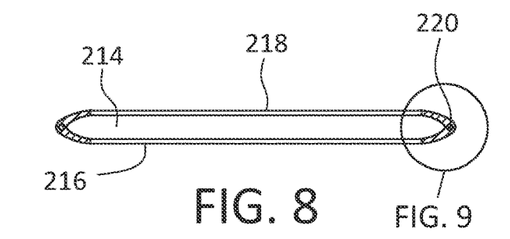
FIG. 8 is a cross-sectional view of the new and improved exchangeable lens platform (ELP) as shown in FIG. 5, and as taken along the lines 8-8 of FIG. 5.
Figure 9:
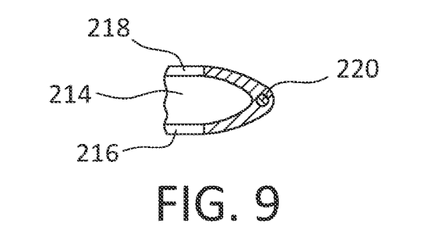
FIG. 9 is an enlarged view of the encircled region 9 as shown in FIG. 8 showing the superior and inferior arcuate portions and the flexible memory strip.

Continuing further, and with reference being made to FIGS. 5 and 7, the new and improved exchangeable lens platform (ELP) 200 is adapted to have a memory strip 220 incorporated therein. The memory strip 220 extends around substantially the entire angular extent of the new and improved exchangeable lens platform (ELP) 200 and provides the new and improved exchangeable lens platform (ELP) 200 with its normal horseshoe shape or configuration as can best be appreciated from FIG. 5. The memory strip can be fabricated from any suitable medically approved metal or alloy, or other materials exhibiting the desired qualities of, for example, being flexible, resilient, and having shape-memory properties. Examples of such memory strips are those that are fabricated from Nitinol, polymethyl methacrylate (PMMA), prolene, or polyamide.

Figure 11:
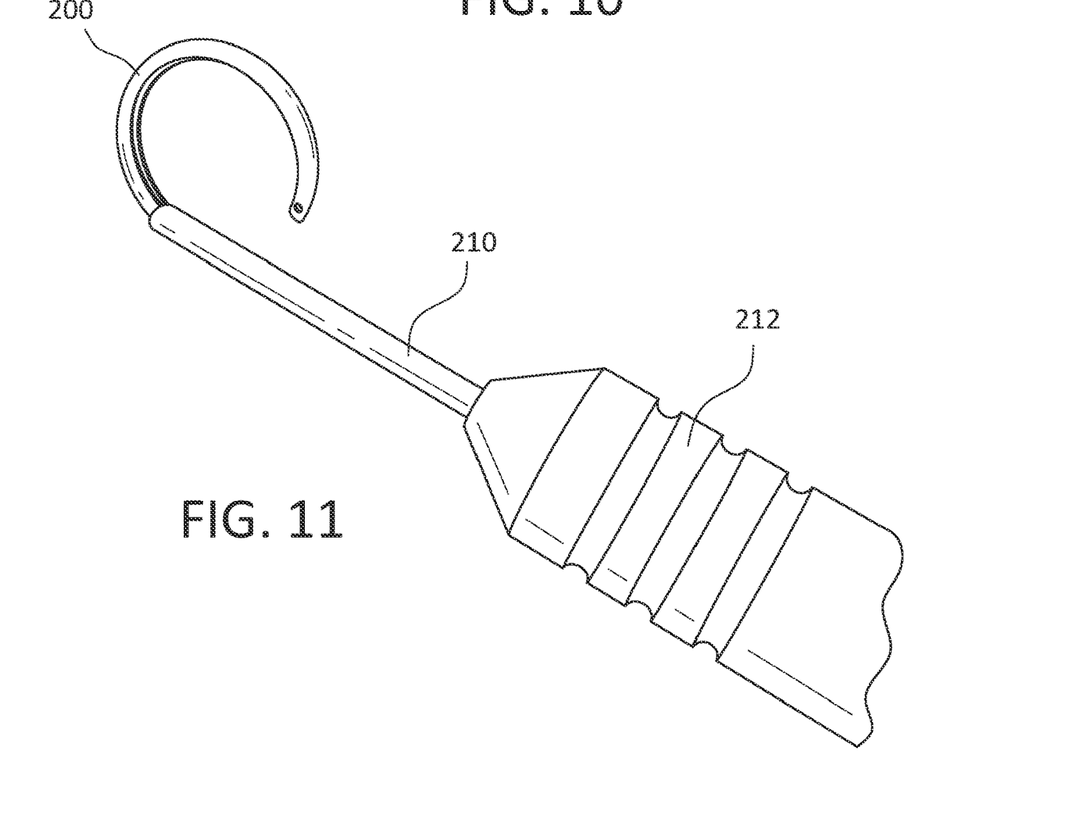
FIG. 11 is a perspective view of an exemplary exchangeable lens platform (ELP) delivery device into which the new and improved exchangeable lens platform (ELP) is inserted and then subsequently delivered by the anterior segment surgeon when the surgeon is ready to insert the new and improved exchangeable lens platform (ELP) into the capsular bag of the human eye.

Having described all of the operative components of the new and improved exchangeable lens platform (ELP) 200, the use of the same will now be described. Prior to inserting the new and improved exchangeable lens platform (ELP) 200 into the capsular bag of the eye, the new and improved exchangeable lens platform (ELP) 200 is firstly inserted into a suitable delivery device 212 as shown in FIG. 11. The delivery device 212 includes a micro-finger, not shown, which is inserted into one of the two apertures 206, 208 of the substantially circular, horseshoe shaped ring member 200 and is retracted into the linearly extending cartridge 210 of the delivery device 212. Then, when the new and improved exchangeable lens platform (ELP) 200 is to be inserted into the capsular bag of the eye, the micro-finger, not shown, is extended so as to move toward the open end of the linearly extending cartridge 210 of the delivery device 212 such that the new and improved exchangeable lens platform (ELP) 200 will be moved out from the open end of the linearly extending bored tube 210 of the delivery device 212. The micro-finger, not shown, may be part of, or attached to, a suitable linear actuator within the delivery device 212. In turn, as the new and improved exchangeable lens platform (ELP) 200 is inserted into the capsular bag 110, the new and improved exchangeable lens platform (ELP) 200, having the substantially circular configuration, will be forced to collapse or fold upon itself at diametrically opposed locations, which have been illustrated by dotted lines in FIG. 5, and which form apex portions of the new and improved exchangeable lens platform (ELP) 200 which have been denoted by reference characters 222, 224.

These apex portions 222, 224 are adapted to be seated within diametrically opposed fornix or equatorial portions of the capsular bag, which can be achieved by suitable manipulation of the new and improved exchangeable lens platform (ELP) 200 relative to the capsular bag. Thereafter, once properly seated within the capsular bag of the eye, the surgeon can manipulate the delivery device 212 so as to effectively disengage the micro-finger, not shown, from the particular one of the apertures 206, 208. In turn, the intraocular lens (IOL) 112 will then be inserted into the new and improved exchangeable lens platform (ELP) 200 such that the haptics components 116, 116 of the intraocular lens (IOL) 112 will be disposed within the track or groove 214 of the new and improved exchangeable lens platform (ELP) 200. The surgeon can then effectively rotate the intraocular lens (IOL) 112 relative to the new and improved exchangeable lens platform (ELP) 200 whereby the haptic components 116, 116 of the intraocular lens (IOL) 112 can be moved into the apex regions 222, 224 of the new and improved exchangeable lens platform (ELP) 200 whereby it will be appreciated that the haptic components 116, 116 of the intraocular lens (IOL) 112 will effectively be captured and prevented from moving either in lateral or circumferential directions within the new and improved exchangeable lens platform (ELP) 200. Accordingly, the intraocular lens (IOL) 112 is mounted within the new and improved exchangeable lens platform (ELP) 200 in a properly oriented and stabilized state within the eye. It is still yet further appreciated that as a result of the haptic components 116, 116 of the intraocular lens (IOL) 112 being disposed within the track or groove 214 of the new and improved exchangeable lens platform (ELP) 200, as opposed to being in direct contact with the inner peripheral walls of capsular bag 110, the haptic components 116, 116 of the intraocular lens (IOL) 112 will not become entangled or enmeshed with tissue growth or fibrosis, during the subsequent healing process, so, accordingly, if need be, the particular intraocular lens (IOL) 112 can be removed and replaced with a different intraocular lens (IOL) 112 as may be required, such as, for example, to provide the patient with an intraocular lens (IOL) 112 having a different curvature or corrective power for the patients vision.

It is lastly noted that in addition to the unique features and medical results that are able to be achieved by means of the present invention, as has been set forth hereinbefore, still other unique features and medical benefits are rendered possible as a result of the use of the exchangeable lens platform (ELP) of the present invention. For example, the use of the exchangeable lens platform (ELP) can help prevent pantoscopic tilt, which can cause unwanted or undesirable optical phenomena. Pantoscopic tilt is considered to be any movement of the intraocular lens (IOL) which occurs out of the plane within which the intraocular lens (IOL) is disposed, such plane being defined by X and Y axes. Still further, after the anterior segment surgeon removes the original crystalline lens and inserts an intraocular lens (IOL) into the capsular bag, the haptic components of the intraocular lens (IOL) can impress diametrically opposite forces upon the capsular bag. In some cases, this can lead to the creation of capsular striae upon the posterior capsule. These capsular striae can be very annoying to a post-operative patient because the patient "sees" optical streaks. By using the exchangeable lens platform (ELP) of the present invention, since the exchangeable lens platform (ELP) engages the internal wall portions of the capsular bag in a substantially continuous circumferential or peripheral manner, any forces that may be developed as a result of the exchangeable lens platform (ELP) engaging the internal wall portions of the capsular bag will effectively be uniformly distributed around the capsular bag such that the aforenoted capsular striae will not be developed. Lastly, posterior capsular fibrosis is a common and optically debilitating occurrence after cataract surgery. By using the exchangeable lens platform (ELP) of the present invention, where the exchangeable lens platform (ELP) is placed within the fornix region of the capsular bag, which is where lens epithelial cells tend to propagate and proliferate, the exchangeable lens platform (ELP) will tend to retard their production and subsequent migration.

Obviously, many variations and modifications of the present invention are possible in light of the above teachings. It is therefore to be understood that within the scope of the appended claims, the present invention may be practiced otherwise than as specifically described herein.

What is claimed, and desired to be protected by Letters Patent, is:

1. An exchangeable lens platform (ELP) for use in mounting or fixing an intraocular lens (IOL) within a capsular bag of an eye, comprising:
    a substantially circular, horseshoe shaped ring member which defines a substantially circular locus and which is discontinuous such that said substantially circular, horseshoe shaped ring member is flexible so as to be capable of being diametrically contractible so as to be inserted into a capsular bag of an eye and yet being diametrically expandable so as to engage inner peripheral wall portions of capsular bags having different sizes and dimensions once said substantially circular, horseshoe shaped ring member has been inserted into the capsular bag; and
    a memory strip incorporated within said substantially circular, horseshoe shaped ring member for providing said substantially circular, horseshoe shaped ring member with a predetermined shape and configuration as well as for providing diametrically opposed portions of said substantially circular, horseshoe shaped ring member with radially outwardly oriented biasing forces such that after said substantially circular, horseshoe shaped ring member has been contracted so as to permit said substantially circular, horseshoe shaped ring member to be inserted into a capsular bag of an eye, said diametrically opposed portions of said substantially circular, horseshoe shaped ring member will move radially outwardly, beyond said substantially circular locus of the remainder of the substantially circular, horseshoe shaped ring member, so as to engage diametrically opposed internal fornix wall portions of the capsular bag.

2. The exchangeable lens platform (ELP) as set forth in claim 1, wherein:
    said memory strip is fabricated from a material selected from the group comprising Nitinol, polymethyl methacrylate (PMMA), prolene, and a polyamide.

3. The exchangeable lens platform (ELP) as set forth in claim 1, wherein:
    said substantially circular, horseshoe shaped ring member is fabricated from a material selected from the group comprising a polyamide, an acrylic, a medical grade, FDA-approved material, and a silicone material.

4. The exchangeable lens platform (ELP) as set forth in claim 1, wherein:
    said substantially circular, horseshoe shaped ring member has a groove or track defined upon the inner periphery thereof within which haptic components of an intraocular lens (IOL) are to be disposed such that the intraocular lens (IOL) can be securely mounted upon said substantially circular, horseshoe shaped ring member.

5. The exchangeable lens platform (ELP) as set forth in claim 4, wherein:
    said groove or track defined upon said inner periphery of said substantially circular, horseshoe shaped ring member accommodates the haptic components of an intraocular lens (IOL) such that the haptic components of the intraocular lens (IOL) do not engage internal wall portions of the anterior or posterior portions of the capsular bag, so as to permit the intraocular lens (IOL) to be removed from said substantially circular, horseshoe shaped ring member, and replaced with a different intraocular lens (IOL), as a result of not encountering or becoming entangled with tissue growth and capsular fibrosis.

6. The exchangeable lens platform (ELP) as set forth in claim 4, wherein:
said substantially circular horseshoe-shaped ring member is flexible and diametrically contractible so as to be capable of being inserted into a capsular bag of an eye, said diametrically contractible portions of said substantially circular horseshoe-shaped ring member forming upper and lower arcuate sections connected together by diametrically opposed pivotal portions so as to be inserted into diametrically opposed fornix portions of the capsular bag and within which the haptic components of the intraocular lens (IOL) will be engaged, whereby the haptic components of the intraocular lens (IOL) will effectively be captured within said groove or track so as not to be capable of substantial lateral movement, as well as within said pivotal portions of said substantially circular horseshoe-shaped ring member so as not to be capable of circumferential movement within said track or groove of said substantially circular horseshoe-shaped ring member.

7. The exchangeable lens platform (ELP) as set forth in claim 1, wherein:
said substantially circular horseshoe-shaped ring member subtends an angular expanse of approximately 340°.

8. An exchangeable lens platform (ELP) for use in mounting or fixing an intraocular lens (IOL) within a capsular bag of an eye, comprising:
a substantially circular, horseshoe shaped ring member which defines a substantially circular locus and which is discontinuous such that said substantially circular ring member is flexible so as to be capable of being diametrically contractible so as to be inserted into a capsular bag of an eye and yet being diametrically expandable so as to engage inner peripheral wall portions of capsular bags having different sizes and dimensions once said substantially circular, horseshoe shaped ring member has been inserted into the capsular bag;
said substantially circular, horseshoe shaped ring member has a circumferentially extending groove or track defined upon an inner peripheral portion thereof within which haptic components of an intraocular lens (IOL) are to be disposed so as to engage continuous circumferential portions of said groove or track; and
said flexible and diametrically contractible, substantially circular horseshoe-shaped ring member forms upper and lower arcuate sections connected together by pivotal portions, wherein diametrically opposed portions of said substantially circular horseshoe-shaped ring member are adapted to move radially outwardly, beyond said substantially circular locus of the remainder of the substantially circular, horseshoe shaped ring member, so as to be inserted into diametrically opposed fornix portions of the capsular bag and within which the haptic components of the intraocular lens (IOL) will be engaged, whereby the haptic components of the intraocular lens (IOL) will effectively be captured between said upper and lower arcuate sections of said groove or track so as not to be capable of disengagement from said circumferentially extending groove or track, as well as within said pivotal portions of said substantially circular horseshoe-shaped ring member so as not to be capable of circumferential movement within said track or groove of said substantially circular horseshoe-shaped ring member once said haptic components of the intraocular lens (IOL) have been inserted into said diametrically opposed portions of said substantially circular horseshoe-shaped ring member which are adapted to be disposed within the diametrically opposed fornix portions of the capsular bag.

9. The exchangeable lens platform (ELP) as set forth in claim 8, further comprising:
a memory strip incorporated within said substantially circular, horseshoe shaped ring member for providing said substantially circular, horseshoe shaped ring member with a predetermined shape and configuration as well as for providing said diametrically opposed portions of said substantially circular, horseshoe shaped ring member with radially outwardly oriented biasing forces such that after said substantially circular, horseshoe shaped ring member has been contracted so as to permit said substantially circular, horseshoe shaped ring member to be inserted into a capsular bag of an eye, said diametrically opposed portions of said substantially circular, horseshoe shaped ring member will tend to move radially outwardly so as to engage internal wall portions of the capsular bag.

10. The exchangeable lens platform (ELP) as set forth in claim 9, wherein:
said memory strip is fabricated from a material selected from the group comprising Nitinol and polymethyl methacrylate (PMMA), prolene, and a polyamide.

11. The exchangeable lens platform (ELP) as set forth in claim 8, wherein:
said substantially circular, horseshoe shaped ring member is fabricated from a material selected from the group comprising a polyamide, acrylic, a medical grade, FDA-approved material, and a silicone material.

12. The exchangeable lens platform (ELP) as set forth in claim 8, wherein:
said substantially circular horseshoe-shaped ring member subtends an angular expanse of approximately 340°.

13. An exchangeable lens platform (ELP) for use in mounting or fixing an intraocular lens (IOL) within a capsular bag of an eye, comprising:
a substantially circular, horseshoe shaped ring member which is discontinuous such that said substantially circular ring member is flexible so as to be capable of being diametrically contractible so as to be inserted into a capsular bag of an eye and yet being diametrically expandable so as to engage inner peripheral wall portions of capsular bags having different sizes and dimensions once said substantially circular, horseshoe shaped ring member has been inserted into the capsular bag;
said substantially circular, horseshoe shaped ring member has a circumferentially extending groove or track defined upon the inner periphery thereof within which haptic components of an intraocular lens (IOL) are adapted to be disposed so as to engage continuous circumferential portions of said groove or track; and
said groove or track defined upon said inner periphery of said substantially circular, horseshoe shaped ring member accommodates the haptic components of an intraocular lens (IOL) such that the haptic components of the intraocular lens (IOL) do not engage internal wall portions of the capsular bag, and permits an intraocular lens (IOL) to be removed from said substantially circular, horseshoe shaped ring member and be replaced with a different intraocular lens (IOL) as a result of not encountering or becoming entangled with tissue growth and capsular fibrosis.

14. The exchangeable lens platform (ELP) as set forth in claim 13, further comprising:
    a memory strip incorporated within said substantially circular, horseshoe shaped ring member for providing said substantially circular, horseshoe shaped ring member with a predetermined shape and configuration as well as for providing diametrically opposed portions of said substantially circular, horseshoe shaped ring member with radially outwardly oriented biasing forces such that after said substantially circular, horseshoe shaped ring member has been contracted so as to permit said substantially circular, horseshoe shaped ring member to be inserted into a capsular bag of an eye, said diametrically opposed portions of said substantially circular, horseshoe shaped ring member will tend to move radially outwardly so as to engage internal wall portions of the capsular bag.

15. The exchangeable lens platform (ELP) as set forth in claim 14, wherein:
    said memory strip is fabricated from a material selected from the group comprising Nitinol, polymethyl methacrylate (PMMA), prolene, and a polyamide.

16. The exchangeable lens platform (ELP) as set forth in claim 13, wherein:
    said substantially circular, horseshoe shaped ring member is fabricated from a material selected from the group comprising a polyamide, an acrylic, a medical grade, FDA-approved material, and a silicone material.

17. The exchangeable lens platform (ELP) as set forth in claim 13, wherein:
    said substantially circular horseshoe-shaped ring member subtends an angular expanse of approximately 340°.

18. The exchangeable lens platform (ELP) as set forth in claim 8, wherein:
    said flexible and diametrically contractible, substantially circular horseshoe-shaped ring member, forming said upper and lower arcuate sections and connected together by diametrically opposed pivotal portions so as to be inserted into diametrically opposed fornix portions of the capsular bag and within which the haptic components of the intraocular lens (IOL) will be engaged so as to effectively be captured within said groove or track so as not to be capable of substantial lateral movement, as well as within said pivotal portions of said substantially circular horseshoe-shaped ring member so as not to be capable of circumferential movement within said track or groove of said substantially circular horseshoe-shaped ring member, effectively preventing the intraocular lens (IOL) from experiencing pantoscopic tilt.

19. The exchangeable lens platform (ELP) as set forth in claim 8, wherein:
    said flexible and diametrically contractible, substantially circular horseshoe-shaped ring member, forming said upper and lower arcuate sections and connected together by diametrically opposed pivotal portions so as to be inserted into diametrically opposed fornix portions of the capsular bag and within which the haptic components of the intraocular lens (IOL) will be engaged so as to effectively be captured within said groove or track, effectively prevent the haptic components of the intraocular lens (IOL) from causing capsular striae.

* * * * *